United States Patent [19]

Irving et al.

[11] Patent Number: 4,535,789
[45] Date of Patent: Aug. 20, 1985

[54] TOBACCO ROD FIRMNESS SENSOR

[75] Inventors: Christopher L. Irving, Chesterfield; Jerome S. Osmalov, Richmond, both of Va.

[73] Assignee: Philip Morris, Inc., New York, N.Y.

[21] Appl. No.: 519,605

[22] Filed: Aug. 2, 1983

[51] Int. Cl.³ .................................................. A24C 5/14
[52] U.S. Cl. .................................... 131/84.1; 131/280; 131/906; 131/84.2
[58] Field of Search .................... 131/906, 280, 84 A, 131/84 R

[56] References Cited

U.S. PATENT DOCUMENTS

| 4,033,360 | 7/1977 | Nienow et al. | 131/84 A |
| 4,100,762 | 3/1977 | Strydom | 131/280 |
| 4,413,637 | 11/1983 | Irving | 131/906 |

Primary Examiner—V. Millin

[57] ABSTRACT

A tobacco rod firmness sensor arrangement wherein the tongue of a continuous rod type cigarette making machine is divided into an upstream portion and a downstream portion. The upstream portion is independently mounted from the downstream portion and is associated with a sensor to measure the force exerted by the tobacco rod compressed between the upstream portion and the garniture. Calibration of the sensor is unaffected by adjustment of the downstream portion of the divided tongue.

7 Claims, 5 Drawing Figures

TOBACCO ROD FIRMNESS SENSOR

FIELD OF THE INVENTION

This invention relates to cigarette making machinery and more particularly to an apparatus for providing a continuous output indication of the relative firmness of a tabacco rod during the manufacture of cigarettes.

BACKGROUND

Certain cigarette making machines, such as the Molins Mk8 and Mk9 models, include means for forming a continuous tobacco rod from tobacco filler material and from a continuous length of cigarette paper having a width equal to slightly more than the circumference of the cigarette rod. The cigarette paper is fed onto a moving flexible garniture belt and the tobacco filler is deposited onto the paper. The garniture belt, cigarette paper and filler resting thereon are then formed into a rod shape as they are passed between a tapered concave up garniture positioned below and acting on the lower surface of the belt and an opposed tapered concave down tongue (also referred to in the art as the "short" tongue) positioned above and acting on the filler. As the rod leaves the tongue-garniture area, the edges of the paper are brought together in an overlapping fashion to encompass the filler material. The overlapped edges are adhered, thus completing the formation of the continuous tobacco rod. Downstream, the rod is cut into lengths to form a filterless cigarette. A filter may be added if desired.

To ensure that a desirable firmness of the tobacco rod is obtained, some cigarette making machines incorporate a sensor to detect such firmness. The firmness may be adjusted in response to the sensed firmness by regulating the amount of tobacco filler fed onto the paper.

One such sensor design is shown in Nienow, et al., U.S. Pat. No. 4,033,360, July 5, 1977. The Nienow device provides a strain gauge arrangement fitted on an arm supporting the tongue. As tobacco moves through the garniture area of the cigarette maker, the tobacco is compressed between the garniture and the tongue. The tongue and the arm supporting the tongue are deflected by the compressed tobacco. The degree of deflection corresponds to the rate of tobacco feed and to the resulting tobacco rod firmness. The signal generated by the arrangement is proportional to the degree of deflection and this is indicative of rod firmness. The signal may be calibrated by incrementally regulating the tobacco feed rate to make tobacco rods having a range of firmnesses while noting the corresponding signal value. The firmness of the rods so formed may be accurately measured in the laboratory to establish the signal-firmness correlation.

Another design is shown in Strydom, U.S. Pat. No. 4,010,762, Mar. 8, 1977, wherein the tongue is separated into two portions, the downstream portion being connected by an arm to the upstream portion and a strain gauge being mounted on the arm. As in Nienow, the signal generated by the strain gauge is indicative of rod firmness. A second Strydom arrangement utilizes a segment disposed in an aperture in the concave garniture below the garniture tape. The segment is mounted on an arm having a strain gauge attached thereto.

These prior arrangements suffer the problem of losing the calibration of the strain gauge. This problem is the result of dimensional changes in and between the tongue and garniture. These changes may sometimes arise because the mounting may shift due to vibration or the like. However, more often, these changes arise because positional adjustment of the tongue piece is periodically required to compensate for dimensional changes resulting from the wearing away of the surface of the tongue piece by the tobacco rod components passing thereover and the wearing away of the thickness of the garniture belt from rubbing against the garniture. Wear is particularly severe at the downstream tip of the tongue piece. When the position of the tongue piece is adjusted, the calibration of the strain gauge apparatus must also be redetermined.

This is also true for the second mentioned Strydom arrangement because the segment acts against the tongue through the garniture tape, paper and filler. Moreover, this segment arrangement of Strydom suffers from the additional disadvantage that the firmness properties of the garniture belt, against which the segment acts, directly influence the sensor indication. Thus, any change in such properties caused by belt wear or flexure during belt life directly affects the sensor reading and results in erroneous readings.

Accordingly, there is a need in the art for a sensor arrangement, strain gauge, or otherwise, that does not require adjusting when the tongue is adjusted.

SUMMARY OF THE INVENTION

The present invention alleviates to a great extent the inadequacies of the prior art by providing a tongue divided into an upstream portion and a downstream portion, the upstream portion being independently mounted from the downstream portion and having firmness sensing means associated therewith. Moreover, the upstream portion is mounted to act in opposition to the garniture which is not positionally adjusted during extended normal operation of the cigarette maker. With such an arrangement, adjustment of the downstream portion is sufficient to compensate for component wear and to efficiently maintain proper rod formation. However, such adjustment of the downstream portion in no way affects calibration of the firmness sensing means which is associated solely with the upstream portion. Therefore, the laborious recalibration of the firmness sensor is eliminated.

A further advantage of the invention is that the firmness measurement is affected to a far less degree by wear in the thickness of the garniture belt in that the tobacco is under lower compression at the upstream portion of the tongue than at the downstream portion.

It is an object of the present invention to provide a sensor arrangement for measuring firmness of a tobacco rod as it is formed in a cigarette making machine.

It is another object of the invention to provide a sensor arrangement that does not require recalibration when any other cigarette making machine component, particularly the tongue, is adjusted.

It is a further object of the present invention to provide a sensor arrangement having the foregoing advantages and wherein the tongue is divided into an upstream and a downstream portion, the portions are independently mounted, and the upstream portion has associated therewith sensor means to generate a signal indicative of rod firmness.

Further objects and advantages of the present invention will be readily apparent from the below description and drawings wherein:

DETAILED DESCRIPTION OF THE PREFERRED EMBODIMENT

Figure 1:
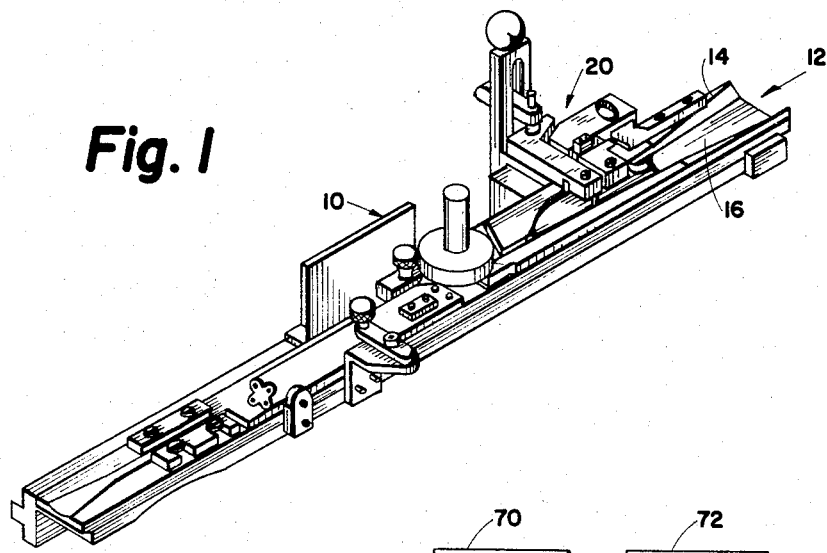
FIG. 1 is a perspective view showing the preferred embodiment of the sensor arrangement of the present invention mounted on a continuous tobacco rod forming portion of a cigarette making machine.

Refer now to FIG. 1 there being shown a preferred embodiment of the present invention in position on the continuous tobacco rod forming portion, generally designated by reference numeral 10, of a Molins Mk8 or Mk9 cigarette making machine. The operation of such machines is well known in the art. Tobacco filler enters garniture 14 in the downstream direction of arrow 12 and is deposited on a continuing strip of cigarette paper riding on garniture tape 16 also moving in the direction of arrow 12. The filler is transferred in and is prevented from escaping garniture 14 by appropriate structure (not shown) positioned thereover. The filler is conveyed by friction with the cigarette paper. As the cigarette paper and filler progress through the garniture, the tapered curved sides of garniture 14 force the edges of tape 16 and thus the cigarette paper to wrap up around the filler as the tongue, generally designated by reference numeral 20, conforms the tobacco filler into a rod shape by means of a tapered concave down trough member. As the rod leaves the tongue-garniture region, the edges of the cigarette paper are adhered.

Figure 2:
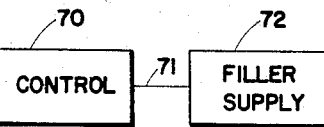
FIG. 2 is a close up perspective view of the sensor arrangement of FIG. 1.
Figure 2:
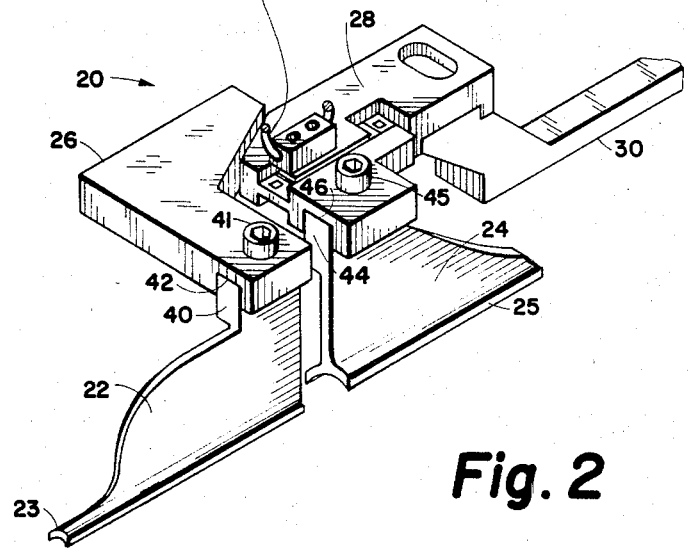

The present invention lies in the unique tongue design, a preferred embodiment of which is illustrated in more detail in FIG. 2. The conventional tongue is modified to be divided into two portions, an upstream portion 24 and a downstream portion 22. Wear of the trough 25 of the tongue is most pronounced at downstream tip 23. The position of tip 23 is crucial to the proper formation of the tobacco rod. When the tongue requires adjusting, it is the critical positioning of tip 23 that is often involved. As discussed above, such tongue adjustment voids the calibration of the firmness sensor apparatus if such apparatus is mounted with or mounted to act opposed to the tongue. In the present invention, tongue 20 is divided into two individually mounted portions. Downstream tip 23 of tongue 20 is associated with the downstream portion 22 and the sensing means is associated with the upstream portion 24. Thus, adjustment of tip 23 in no way affects the calibration of any firmness sensing means associated with upstream portion 24.

Downstream portion 22 is mounted in a conventional manner to maker 10 by clamping of base 26. Downstream portion 22 has shoulder 40 which mates with notch 42 of base 26 and is affixed thereto by bolt 41.

Figure 3:
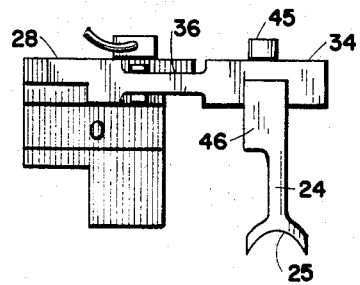
FIG. 3 is an elevation view of the downstream end of the upstream portion of the sensor arrangement of FIG. 1.
Figure 4:
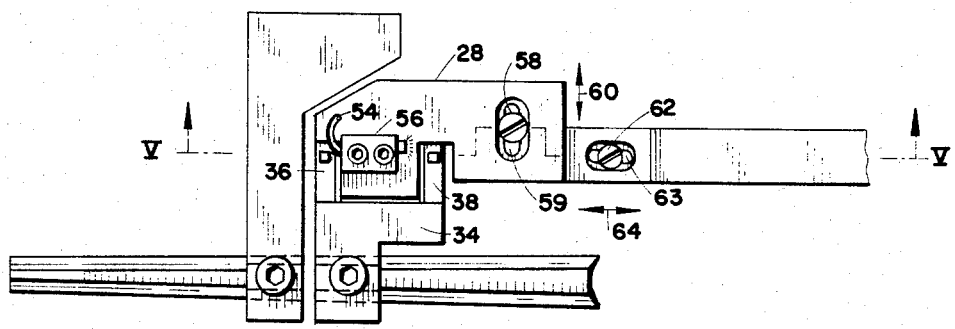
FIG. 4 is a plan view of the sensor arrangement of FIG. 2.
Figure 5:
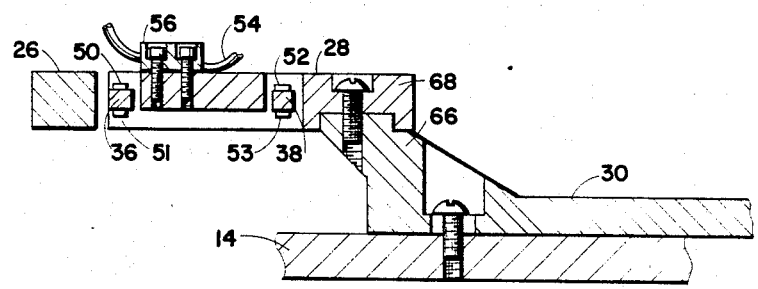
FIG. 5 is a view taken along line V—V of FIG. 4.

Upstream portion 24 is affixed to garniture 14 via base 28 and bracket 30, an elevation view of which is shown in FIG. 3. Shoulder 46 mates with notch 46 of arm 34 of base 28 and is held thereto by bolt 45. Base 28 also includes beams 36 and 38 from which arm 34 and portion 24 are suspended. As shown in FIG. 5, base 28 is affixed to bracket 30 via shoulder 66, notch 68, bolt 58 and slot 59 such that base 28, and thus trough 25, may be adjusted in the direction of arrows 60, of FIG. 4, traverse to the flow of tobacco filler. Similarly, bracket 30 is bolted via a plurality of bolts 62 extending through slots 63 (only one bolt-slot arrangement illustrated) into garniture 14, slots 63 being oriented such that bracket 30 and thus trough 25 is adjustable in the direction of arrows 64 parallel to the direction 12 of the flow of tobacco filler.

Once upstream portion 24 is mounted as described, no further adjustment is necessary during normal cigarette machine operation. Adjustment or replacement of downstream portion 22, such as may be required because of wear of tip 23, does not affect upstream portion 24 positioning or sensor calibration. Moreover, upstream portion 24 is rigidly mounted opposite relatively fixed garniture 14 such that there are no adjustments possible to affect calibration other than at bolts 58 and 62. At normal operating conditions, the only significant movement of upstream portion 24 is in response to force exerted by tobacco filler, cigarette paper and garniture belt compressed between upstream portion 24 and garniture 14. This movement of portion 24 results in the elastic flexure of beams 36 and 38. Strain gauges 50, 51, 52 and 53 are mounted to beams 36 and 38 and wires (not shown) interconnect the strain gauges in a known manner, such as disclosed in Nienow, to provide a signal indication of tobacco rod firmness as a function of such flexure of beams 36 and 38. Cable 54, affixed to base 28 via clamp 56, and includes a number of wires to carry the signal to control means 70 which interprets the signal and sends a corrective signal as necessary via cable 71 to tobacco filler supply means 72 to either increase filler supply to make the rod more firm or decrease filler supply to make the rod less firm.

The above discussed strain gauge arrangement is only one means for sensing the force on independently mounted upstream portion 24 exerted by tobacco filler (as well as the cigarette paper and garniture belt 16) compressed between portion 24 and garniture 14 and the present invention is not limited thereto. Other devices may be employed to sense such force within the scope of the present invention.

The above description and drawings are only illustrative of a preferred embodiment which achieves the objects, features and advantages of the present invention and it is not intended that the present invention be limited thereto. Any modification of the present invention which comes within the spirit and scope of the following claim is considered part of the present invention.

What is claimed as new and desired to be secured by Letters Patent of the United States is:

1. In a cigarette making machine of a type having means for forming, from tobacco filler and tobacco paper, a continuous tobacco rod between a tapered concave garniture and a tapered concave tongue, the improvement comprising: the tongue being divided into an upstream portion and a downstream portion; said portions being independently mounted to said machine; and, sensing means for measuring the force exerted on said upstream portion by the filler compressed between said upstream portion and the garniture and for providing an indication of the force.

2. The invention as in claim 1 wherein a portion of the garniture positioned opposed to said upstream tongue portion is essentially static during normal operation of the machine.

3. An apparatus for sensing the firmness of a tobacco rod in a garniture area of a cigarette making machine comprising: a tongue divided into an upstream portion and a downstream portion, said portions being independently mounted; sensing means associated with said upstream portion for sensing the force exerted on said upstream portion.

4. A method for making a continuous tobacco rod comprising the steps of: providing a cigarette making machine of a type having means for forming, from tobacco filler and tobacco paper, a continuous tobacco rod between a tapered concave garniture and a tapered concave tongue, the tongue being divided into an upstream portion and a downstream portion, the portions being independently mounted to the machine, sensing means for measuring and for providing an indication of the force exerted on the upstream portion by the filler compressed between the upstream portion and the garniture and filler supply means for controllably supplying a flow of tobacco filler between the garniture and tongue at a variable rate; providing tobacco filler and cigarette paper; operating said machine and feeding thereto said tobacco filler and said cigarette paper; calibrating the indication of said sensing means to the firmness of the continuous tobacco rod; controlling said filler supply means to vary supply rate of tobacco filler in response to the indication of said sensing means to control the firmness of the continuous tobacco rod.

5. The invention as in claim 1 wherein said sensing means include deflection sensor means for sensing the positional deflection of the tongue.

6. The invention as in claim 5 wherein said upstream tongue portion is mounted to said machine by means of an arm and said deflection sensor means includes at least one strain gauge mounted to said arm.

7. The invention as in claim 1 further comprising control means for receiving said indication of said sensing means and, in response thereto, controlling filler supply means to vary the flow rate of tobacco filler between the garniture and tongue to achieve a desired firmness.

* * * * *